(12) United States Patent
Simnacher

(10) Patent No.: US 7,867,178 B2
(45) Date of Patent: Jan. 11, 2011

(54) APPARATUS FOR GENERATING SHOCK WAVES WITH PIEZOELECTRIC FIBERS INTEGRATED IN A COMPOSITE

(75) Inventor: Erwin Simnacher, Reichenau (DE)

(73) Assignee: SANUWAVE, Inc., Alpharetta, GA (US)

( * ) Notice: Subject to any disclaimer, the term of this patent is extended or adjusted under 35 U.S.C. 154(b) by 1319 days.

(21) Appl. No.: 10/779,696

(22) Filed: Feb. 18, 2004

(65) Prior Publication Data
US 2004/0167445 A1  Aug. 26, 2004

(30) Foreign Application Priority Data
Feb. 26, 2003  (CH) .................................... 0299/03

(51) Int. Cl.
*A61H 1/00* (2006.01)
(52) U.S. Cl. .......................................... 601/2; 367/189
(58) Field of Classification Search ................ 601/1, 601/2, 4; 367/180, 189; 600/439
See application file for complete search history.

(56) References Cited

U.S. PATENT DOCUMENTS

| | | | |
|---|---|---|---|
| 4,858,597 A * | 8/1989 | Kurtze et al. .................... 601/4 |
| 5,058,590 A * | 10/1991 | Wurster ........................ 600/439 |
| 5,101,133 A | 3/1992 | Schäfer |
| 5,111,805 A | 5/1992 | Jaggy et al. |
| 5,119,801 A * | 6/1992 | Eizenhoefer et al. ............ 601/4 |
| 5,131,392 A * | 7/1992 | Jolesz et al. ................. 600/410 |
| 5,869,189 A * | 2/1999 | Hagood et al. ............... 428/461 |
| 5,950,291 A | 9/1999 | Gentilman et al. |
| 5,958,466 A * | 9/1999 | Ong ............................ 425/127 |
| 6,471,662 B1 * | 10/2002 | Jaggy et al. ..................... 601/2 |
| 7,048,699 B2 * | 5/2006 | Ein-Gal ......................... 601/2 |
| 2002/0063495 A1 | 5/2002 | Brenner et al. |
| 2002/0133099 A1 * | 9/2002 | Ein-Gal ......................... 601/2 |

FOREIGN PATENT DOCUMENTS

EP  0 351 015 A2  1/1990
WO  WO 99/48621  9/1999

\* cited by examiner

*Primary Examiner*—Brian Casler
*Assistant Examiner*—Parikha S Mehta
(74) *Attorney, Agent, or Firm*—Hunton & Williams LLP

(57) ABSTRACT

Apparatus for Generating Shock Waves directed at an area of a human or animal body to be treated using piezoelectric fibers, for generating shock waves. The piezofibers integrated in a composite material are controlled for this, and together with a control unit they form the shock-wave generating part.

19 Claims, 3 Drawing Sheets

APPARATUS FOR GENERATING SHOCK WAVES WITH PIEZOELECTRIC FIBERS INTEGRATED IN A COMPOSITE

CROSS-REFERENCE TO RELATED APPLICATION

This application claims priority to and the benefit of Swiss Patent Application No. 2003 0299/03 filed on Feb. 26, 2003, the entire content of which is incorporated herein by reference.

BACKGROUND OF THE INVENTION

The invention relates to an apparatus for generating shock waves directed at an area of a human or animal body to be treated using piezoelectric fibers. The piezofibers integrated in a composite material are controlled for this, and together with a control unit they form the shock-wave generating part.

Shock waves are used for different purposes in human and veterinary medicine. A medical use of these apparatuses in human medicine is lithotripsy, where the generated shock waves are focused on internal objects to be destroyed, such as kidney stones. Further applications are, for instance, inducing of bone growth, treatment of orthopaedically painful diseases (epicondylitis, calcified shoulder) and treatment of nerves, muscles and other soft-tissue structures.

The generation of shock waves using piezoelectric ceramic elements is generally known, for instance from U.S. Pat. No. 5,101,133. A multitude of piezoelectric ceramic elements are arranged on a spherical calotte and form an electro-acoustic transducer.

The arrangement of this multitude of piezoelectric ceramic elements of the known apparatus is very complex and costly as regards their production.

The piezoelectric ceramic elements are embedded in a casting compound of for instance an epoxy resin mixture.

Since the radiating surface of the piezoelectric ceramic elements covers an area of several square millimeters up to some square centimeters, the deformation of the piezoelectric ceramic elements leads to a high strain of the casting compound on the boundary layer to the ceramic elements.

Generally, the miniaturization of the structural shape of the shock-wave generating apparatus is aimed at.

This aim is pursued in order to simplify the handling of the apparatuses, on the one hand, and to open up new applications, for instance for the treatment of salivary stones, on the other hand.

In addition, it is desirable to focus the shock waves on areas having a different geometry. Freely selectable geometric forms of the shock-wave generating systems are required for this. A high efficiency for special applications is reached in this way, for instance for the treatment of long bone-fissures or cellulites.

In view of the above embodiment the invention is based on the task to provide an apparatus for generating shock waves of the type mentioned, which may be manufactured simply and cost-effectively and which may be designed reliably concerning its application and more flexibly as regards its size.

BRIEF SUMMARY OF THE INVENTION

The underlying idea of the invention is to use piezoelectric fibers, hereinafter called piezofibers, for generating shock waves. The essential thought of the invention is that the piezofibers are integrated in a composite material. They are controlled with a control unit and together with said control unit they form the shock-wave generating part.

Piezofibers are known for the use in the aviation industry, especially for the use as impact sensors that may be integrated in the skin of an aircraft wing in conformity with the structure. They are used for the detection of small impact events such as a bird's impact.

For the generation of the shock waves the indirect piezoelectric effect of the fiber materials is used.

An external electric field exerts opposite forces on the positively and negatively charged ions in the crystal lattice. This leads to a deformation of the fiber materials. The piezofibers stretch mainly in their lengthwise direction.

This short stretch is used for generating shock waves in the apparatus according to the invention.

Preferably, the piezofibers are integrated in the composite material such that their lengthwise direction shows to the area to be treated and/or to the shock wave's direction of propagation. In this way a high energy density in the focus range may be achieved.

The piezofibers may be embedded in the composite material in a simple and uniformly distributed way. Thus, the connection of the piezofibers with the composite material is homogeneous.

The contacting of the piezofibers may be realized by a common electrically conductive layer according to the interconnection requirements. Hence, the complex interconnection of a multitude of piezoelectric ceramic elements of the known electro-acoustic transducers is no longer required.

The piezofibers integrated in the composite material form at least one module with the composite material.

This at least one module may form a special unit in a preferred embodiment of the apparatus according to the invention. However, it is also imaginable that the at least one module forms a unit by means of common electrically connected piezofibers.

Furthermore, the piezofibers may be put in curved structures. In both embodiments mentioned above the at least one module may be designed in geometrically different forms.

This facilitates a high flexibility in the embodiment of the shock-wave generating apparatus. Hence, apparatuses for generating shock waves of different geometric forms may be realized.

Additionally, several modules may be arranged next to one another. The modules may be interconnected individually, in groups or with one another.

In order to achieve a compact arrangement of the shock-wave generating apparatus, the at least one module is preferably arranged on a carrier.

The individual piezofibers may be designed in a commonly contacted way on the respective terminals in a separate embodiment. If the module carrier is designed in an electrically conductive way, one of the two contacts may be connected with the module carrier.

The module carrier may have different geometric forms.

The above mentioned preferred variation of the apparatus according to the invention for generating shock waves concerning the geometry allows for the possibility of a miniaturization of the apparatus. This enables the production of small-sized shock-wave generating apparatuses of the mentioned type for intracorporal applications.

Plane modules with piezofibers integrated in the composite material with any shaping may be manufactured.

Hence, for special applications not only smaller shock-wave generating apparatuses may be realized with the apparatus according to the invention but also plane shock-wave generating apparatuses with different focus geometries.

BRIEF DESCRIPTION OF THE DRAWING

These and other features, aspects and advantages of the present invention will become better understood with reference to the following description, appended claims, and accompanying drawing, where:

Figure 1:
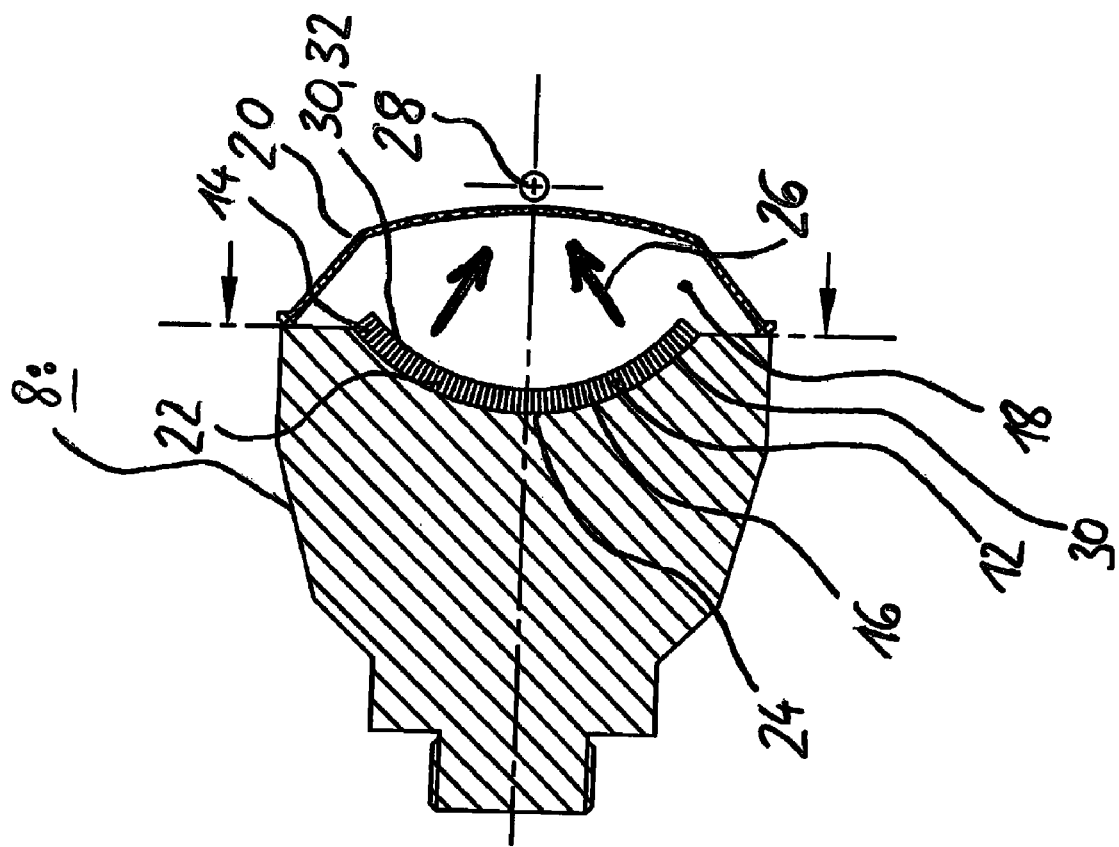
FIG. 1 shows a side and a front view of a preferred embodiment of the invention.
Figure 1:
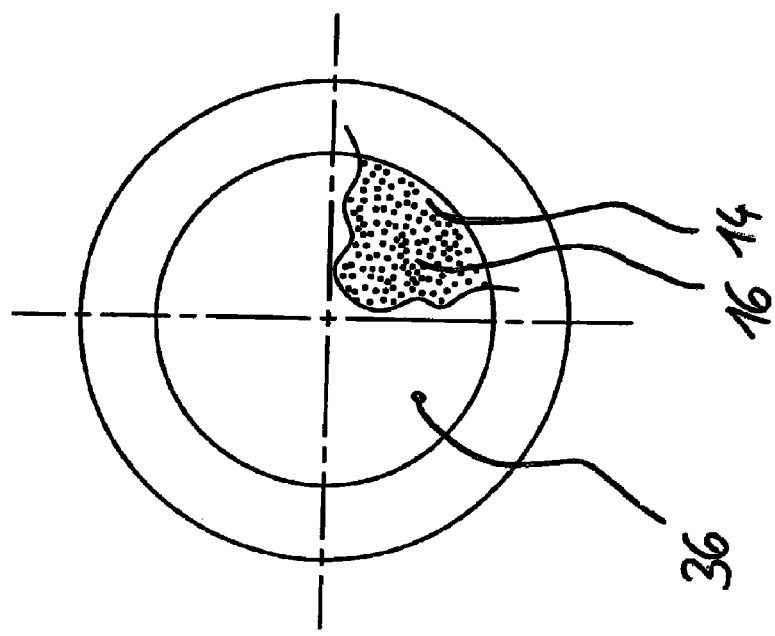

LIST OF REFERENCE NUMBERS 8 shock-wave generating apparatus
12 shock-wave generating part
14 piezofibers
16 composite material
18 medium suitable for the shock-wave transmission
20 coupling membrane
22 module
24 module carrier
26 direction of propagation of the shock waves
28 shock-wave focus
30 respective terminals
32 shock wave on a frontal area of the piezofibers
34 focus line
36 radiating surface of the module
38 module group Equivalent parts are indicated by the same reference numbers.

DETAILED DESCRIPTION OF THE INVENTION

The invention summarized above and defined by the enumerated claims may be better understood by referring to the following detailed description, which should be read in conjunction with the accompanying drawing. This detailed description of a particular preferred embodiment, set out below to enable one to practice the invention, is not intended to limit the enumerated claims, but to serve as a particular example thereof.

FIG. 1 illustrates a shock-wave generating apparatus 8 showing a shock-wave generating part 12 and a medium 18 suitable for the shock-wave transmission which fills a volume between the shock-wave generating part 12 and a coupling membrane 20. As a medium 18 suitable for the shock-wave transmission water or a gel is used, for instance. The coupling membrane 20 serves the energetically low-loss coupling of the shock-wave generating apparatus 8 to a part of the body to be treated.

The shock waves are generated by the shock-wave generating part 12 and propagate in the illustrated direction 26.

Based on the given geometry of the shock-wave generating part 12 they are bundled in a shock-wave focus 28. The shock-wave focus 28 is the area with the highest energy density. In the embodiment illustrated in FIG. 1 the shock-wave generating part 12 is designed in the form of a spherical segment. This leads to a focusing of the shock wave. Focusing may be realized in the known, thus not to be specified, electronic way.

The shock-wave generating part 12 consists of piezofibers 14 integrated in a composite material 16. The piezofibers 14 are electrically connected on the respective terminals 30 and high voltage is applied. High voltage is preferably applied in a pulse-shaped way.

The piezofibers 14 are integrated in the composite material 16 such that they preferably show to the direction of propagation of the shock waves 26 in their lengthwise direction, since they mainly propagate in this direction and may thus reach the highest lift.

This short stretch of the piezofibers 14 is used for generating shock waves in the apparatus according to the invention. If a high-voltage pulse is applied to the piezofibers 14, the piezofibers 14 stretch triggering off a shock wave on a frontal area 32 of the piezofibers 14. The generated shock wave is bundled in a shock-wave focus 28 according to the geometry of the shock-wave generating part 12.

The composite material 16 forms a spatial unit, hereinafter called module, with the integrated fibers 14 in the illustrated embodiment. The module 22 in the geometric form of a spherical segment is arranged on a carrier 24.

The piezofibers 14 are designed in a commonly contacted way on their respective terminals 30 and they are each connected via incoming cables with a control device which is not illustrated herein.

In an especially preferred embodiment of the apparatus according to the invention the module 22 is arranged on an electrically conductive module carrier 24 which is connected in an electrically conductive way with one of the two connections, not illustrated herein, of the terminals 30, commonly contacted each, of the piezofibers 14.

As already specified above the geometry of the shock-wave focus 28 may be determined by the shaping of the module carrier 24 and the module 22.

In the illustrated first embodiment in FIG. 1 a shock-wave focus is generated in the form of an ellipsoid.

Figure 2:
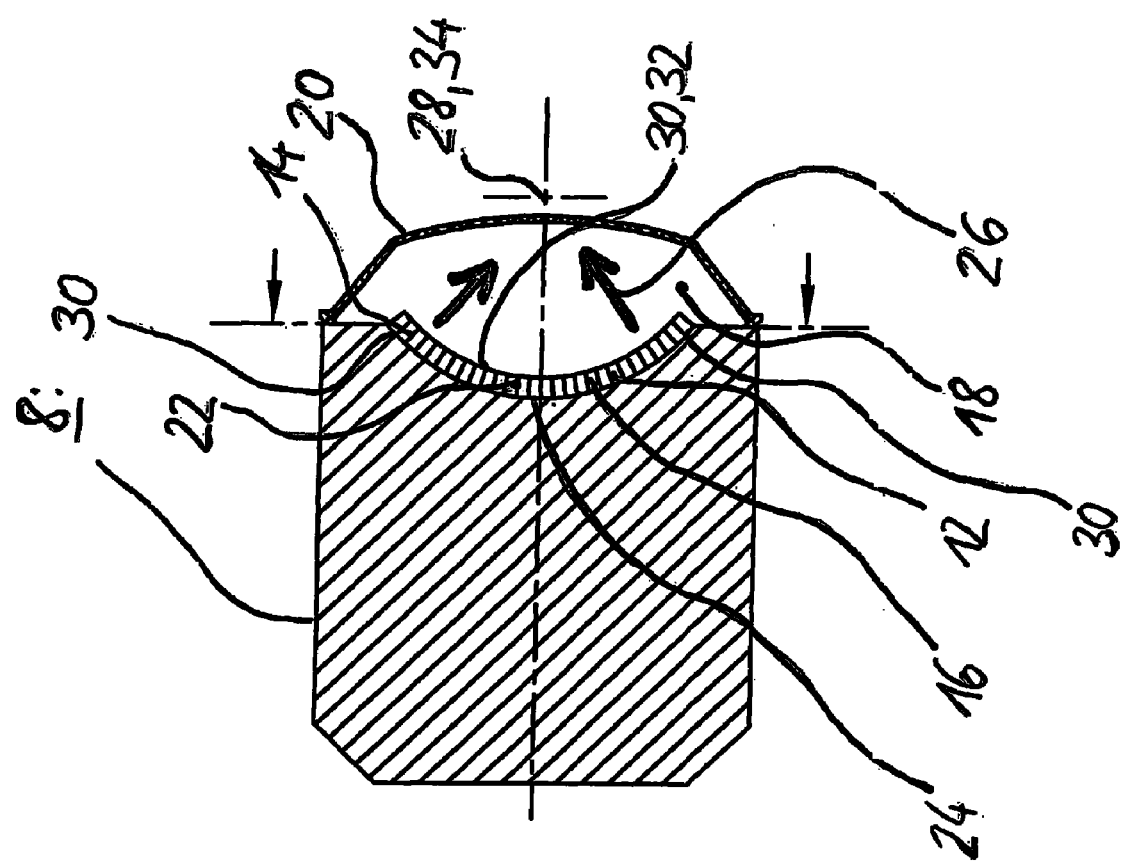
FIG. 2 shows a side and a front view of a further embodiment of the invention and FIG. 3 shows front view of an embodiment of the invention with several modules arranged next to one another.
Figure 2:
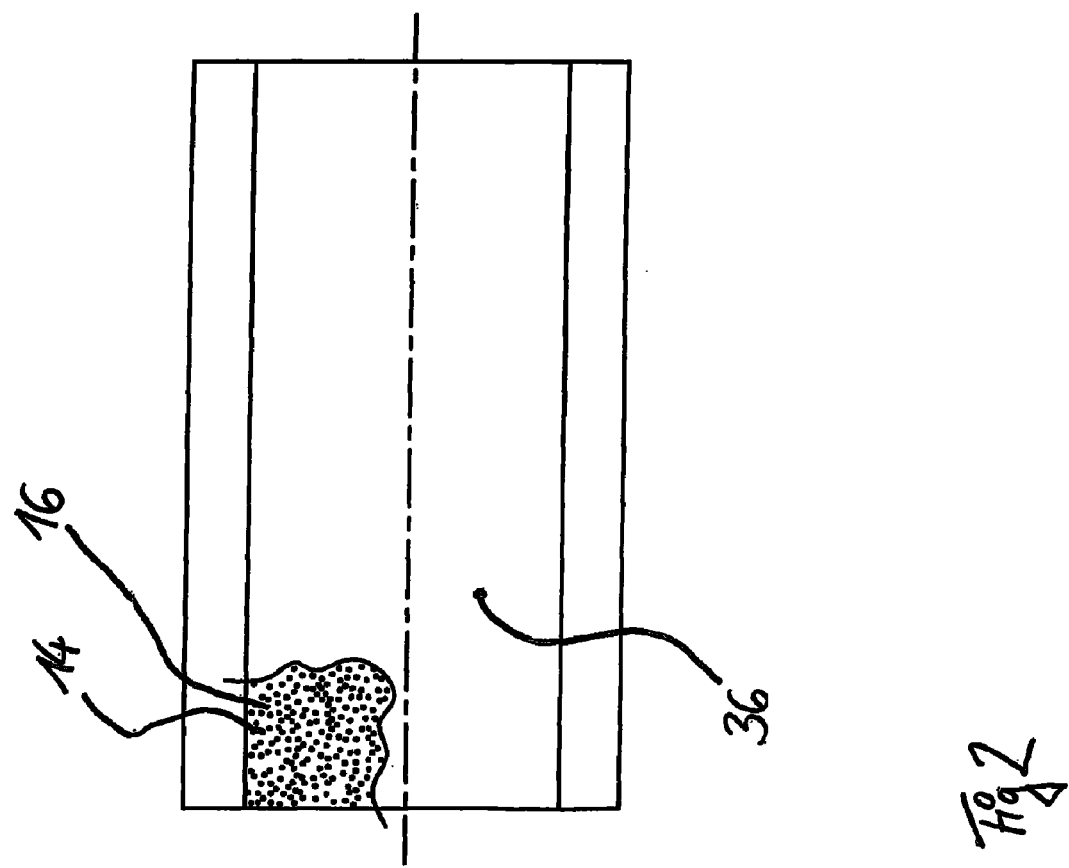

In the illustrated second embodiment shown in FIG. 2 a horizontal cylindrical focus line 34 is generated. For this, the shock-wave generating part 12 is designed geometrically in the form of a pipe segment.

Figure 3:
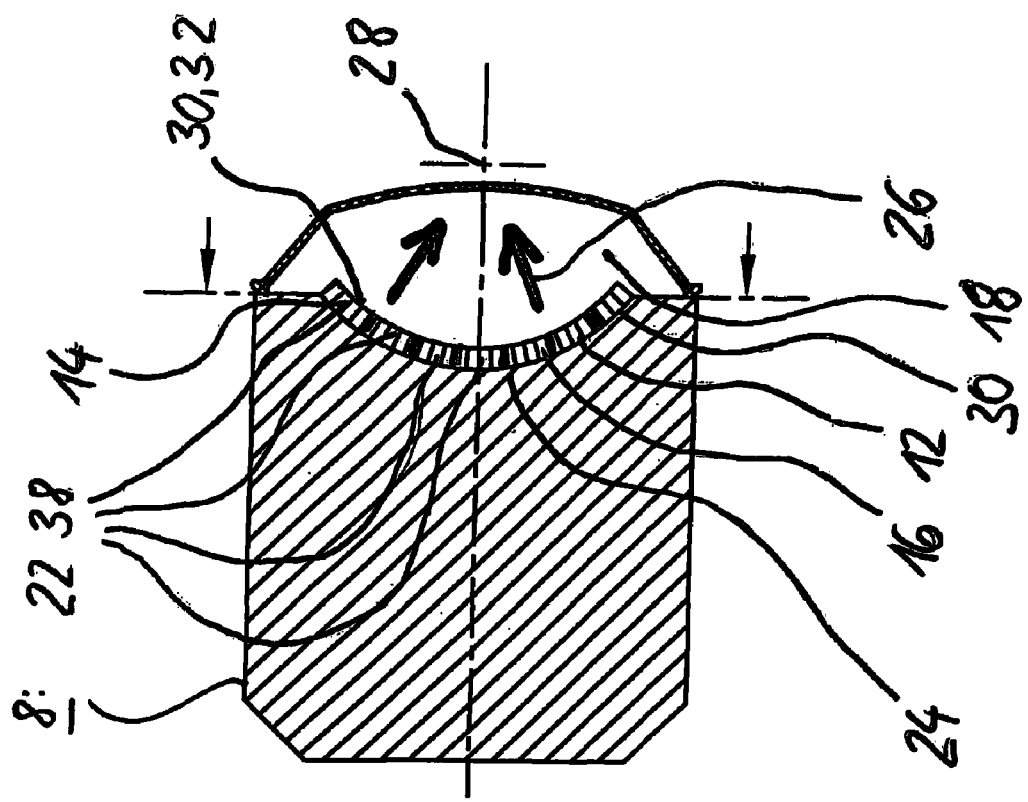
Figure 3:
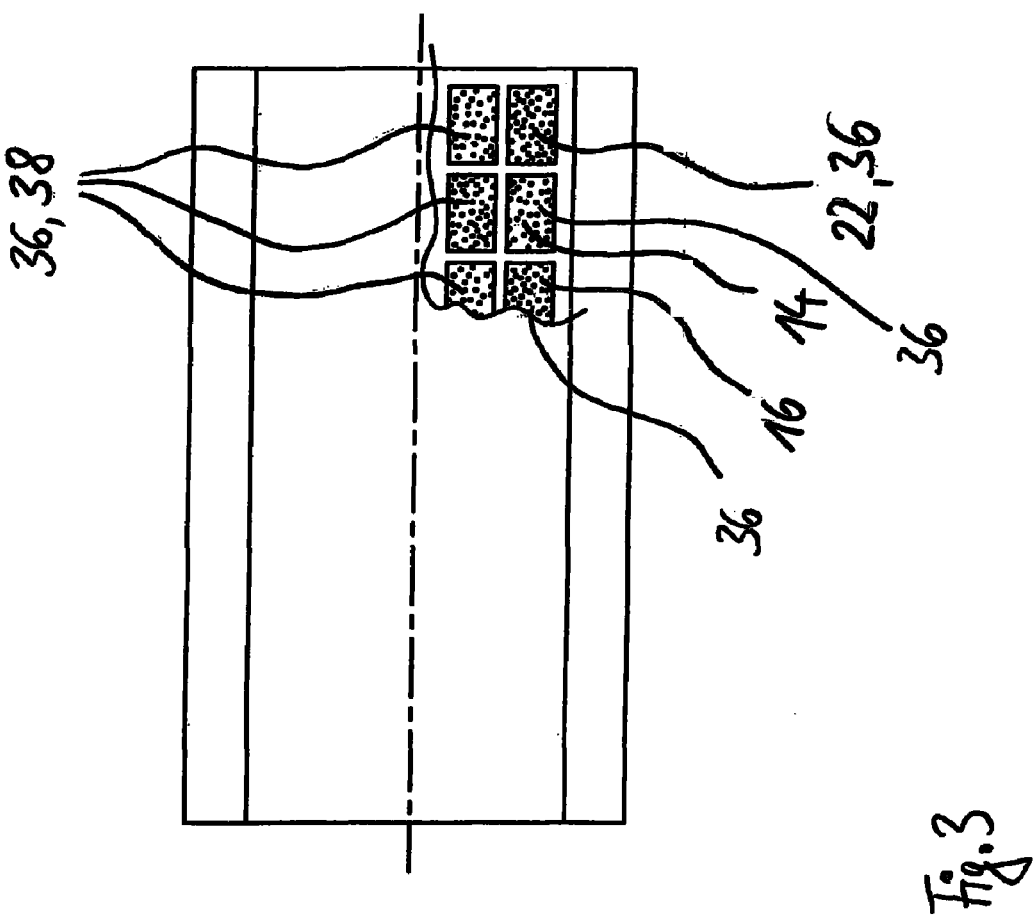

According to a preferred embodiment of the invention as illustrated in FIG. 3, several modules may be arranged next to one another. The individual modules 22 may have different sizes and different forms as regards their radiating surface 36. The modules 22 may be individually controlled. A mutually delayed control of the individual modules 22 may be achieved in this way, for instance. However, they may also be interconnected and controlled in module groups 38.

High voltage is applied in a known way by a high-voltage pulse generator the first pole of which is connected to one terminal 30 of the commonly contacted piezofibers 14 and the second pole of which is connected to the other terminal 30 of the commonly contacted piezofibers 14.

In a preferred embodiment the common terminal 30 of the piezofibers 14 on the module carrier 24 is connected with the preferably electrically conductive carrier material 24.

The module carrier 24 may thus be directly connected to a pole of the high-voltage pulse generator.

What is claimed is:

1. An apparatus for generating shock waves directed at an area of a human or animal body to be treated comprising a plurality of separate piezoelectric modules arranged next to one another on a carrier wherein each module is a spatial unit and includes a plurality of piezoelectric fibers distributed and integrated lengthwise between respective electrical terminals in a continuous composite material between the plurality of piezoelectric fibers, a voltage source electrically connected to at least one electrical terminal and a coupling membrane defining a volume filled with a shock wave transmission medium between the piezoelectric fibers and the coupling membrane, wherein said piezoelectric fibers point toward the coupling membrane.

2. The apparatus according to claim 1, wherein at least two of the plurality of separate piezoelectric modules are electrically interconnected and controllable as a module group apart from one or more other module groups comprised of other modules from the plurality of separate piezoelectric modules.

3. The apparatus of claim 2, wherein the carrier is a pipe-shaped cylindrical segment with the plurality of separate piezoelectric modules arranged providing a horizontal cylindrical focus line.

4. The apparatus of claim 2, wherein at least two of the plurality of separate piezoelectric modules have different sizes from one another.

5. The apparatus of claim 4, wherein the at least two of the plurality of separate piezoelectric modules of different sizes have different forms of radiating surfaces.

6. The apparatus of claim 2, wherein at least two of the plurality of separate piezoelectric modules have different forms of radiating surfaces.

7. The apparatus according to claim 1, wherein at least two of the plurality of separate piezoelectric modules are electrically individually controllable.

8. The apparatus of claim 7, wherein at least two of the plurality of separate piezoelectric modules have different sizes from one another.

9. The apparatus of claim 8, wherein the at least two of the plurality of separate piezoelectric modules of different sizes have different forms of radiating surfaces.

10. The apparatus of claim 7, wherein at least two of the plurality of separate piezoelectric modules have different forms of radiating surfaces.

11. The apparatus according to claim 1, wherein said carrier includes a geometry selected from the group consisting of planar, spherical and cylindrical.

12. The apparatus of claim 11, wherein the carrier is a pipe-shaped cylindrical segment with the modules arranged providing a horizontal cylindrical focus line.

13. The apparatus of claim 12, wherein at least two of the plurality of separate piezoelectric modules have different sizes from one another.

14. The apparatus of claim 13, wherein the at least two of the plurality of separate piezoelectric modules of different sizes have different forms of radiating surfaces.

15. The apparatus of claim 12, wherein at least two of the plurality of separate piezoelectric modules have different forms of radiating surfaces.

16. The apparatus of claim 11, wherein at least two of the plurality of separate piezoelectric modules are at least one of electrically interconnected and controllable as a module group apart from one or more other module groups comprised of other modules from the plurality of separate piezoelectric modules and electrically individually controllable.

17. The apparatus of claim 1, wherein at least two of the plurality of separate piezoelectric modules have different sizes from one another.

18. The apparatus of claim 17, wherein the at least two of the plurality of separate piezoelectric modules of different sizes have different forms of radiating surfaces.

19. The apparatus of claim 1, wherein at least two of the plurality of separate piezoelectric modules have different forms of radiating surfaces.

* * * * *